US008021418B2

(12) United States Patent
Gerberding et al.

(10) Patent No.: US 8,021,418 B2
(45) Date of Patent: Sep. 20, 2011

(54) SANDWICHED RADIOPAQUE MARKER ON COVERED STENT

(75) Inventors: Brent C. Gerberding, Sunnyvale, CA (US); Bavesh Mistry, Cupertino, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/600,022

(22) Filed: Jun. 19, 2003

(65) Prior Publication Data

US 2005/0004653 A1   Jan. 6, 2005

(51) Int. Cl.
*A61F 2/06* (2006.01)

(52) U.S. Cl. ............... 623/1.34; 623/1.13; 623/1.15; 623/1.16

(58) Field of Classification Search .......... 623/1.13, 623/1.15, 1.16–1.21, 1.34, 1.44, 23.64, 23.7
See application file for complete search history.

(56) References Cited

U.S. PATENT DOCUMENTS

| | | | | |
|---|---|---|---|---|
| 5,091,205 A | | 2/1992 | Fan ................... | 427/2 |
| 5,104,404 A | * | 4/1992 | Wolff ................ | 623/1.16 |
| 5,674,241 A | | 10/1997 | Bley et al. ........ | 606/198 |
| 5,683,450 A | | 11/1997 | Goicoechea et al. .. | 623/1 |
| 5,700,285 A | | 12/1997 | Myers et al. .......... | 623/1 |
| 5,707,386 A | * | 1/1998 | Schnepp-Pesch et al. | 606/194 |
| 5,735,892 A | | 4/1998 | Myers et al. .......... | 623/1 |
| 5,749,880 A | | 5/1998 | Banas et al. ........ | 606/198 |
| 5,824,043 A | * | 10/1998 | Cottone, Jr. .......... | 623/1.13 |
| 5,824,046 A | | 10/1998 | Smith et al. .......... | 623/1 |
| 5,843,158 A | | 12/1998 | Lenker et al. ........ | 623/1 |
| 5,928,279 A | | 7/1999 | Shannon et al. ....... | 623/1 |
| 5,961,545 A | | 10/1999 | Lentz et al. .......... | 623/1 |
| 6,001,125 A | | 12/1999 | Golds et al. .......... | 623/1 |
| 6,124,523 A | | 9/2000 | Banas et al. ........ | 623/11 |
| 6,139,573 A | | 10/2000 | Sogard et al. ......... | 623/1.13 |
| 6,156,052 A | * | 12/2000 | Richter et al. ........ | 606/191 |
| 6,203,568 B1 | * | 3/2001 | Lombardi et al. ...... | 623/1.13 |
| 6,238,430 B1 | | 5/2001 | Klumb et al. ........ | 623/1.11 |
| 6,241,039 B1 | | 6/2001 | Jarnstrom et al. .... | 180/69.21 |
| 6,331,189 B1 | * | 12/2001 | Wolinsky et al. ..... | 623/1.15 |
| 6,355,063 B1 | | 3/2002 | Calcote ................ | 623/1.42 |
| 6,358,274 B1 | | 3/2002 | Thompson .......... | 623/11 |

(Continued)

FOREIGN PATENT DOCUMENTS

EP 0938879 1/1999

(Continued)

OTHER PUBLICATIONS

An Official Action and English translation from related Japanese Patent Application No. 2006-517112, dated Nov. 24, 2009. 5 pgs.

(Continued)

*Primary Examiner* — David Isabella
*Assistant Examiner* — Suba Ganesan
(74) *Attorney, Agent, or Firm* — Brooks, Cameron & Huebsch, PLLC

(57) ABSTRACT

A stent comprises a tubular framework having an outer surface and an inner surface and a plurality of interconnected struts. An outer covering of PTFE extends along at least a portion of the outer surface of the expandable framework and an inner covering of PTFE extends along at least a portion of the inner surface of the expandable framework. At least a portion of the inner and outer coverings are contiguous with one another. The stent further comprises at least one radiopaque marker disposed between the inner covering and the outer covering.

25 Claims, 4 Drawing Sheets

U.S. PATENT DOCUMENTS

| | | | |
|---|---|---|---|
| 6,361,759 B1 | 3/2002 | Frayne et al. | 424/9.323 |
| 6,364,903 B2 | 4/2002 | Tseng et al. | 623/1.15 |
| 6,383,214 B1 | 5/2002 | Banas et al. | 623/1.14 |
| 6,395,212 B1 | 5/2002 | Solem | 264/230 |
| 6,398,803 B1 | 6/2002 | Layne et al. | 623/1.13 |
| 6,451,047 B2 | 9/2002 | McCrea et al. | 623/1.13 |
| 6,475,235 B1 | 11/2002 | Jayaraman | 623/1.15 |
| 6,488,700 B2 * | 12/2002 | Klumb et al. | 623/1.12 |
| 6,488,701 B1 | 12/2002 | Nolting et al. | 623/1.13 |
| 6,514,283 B2 | 2/2003 | DiMatteo et al. | 623/1.13 |
| 6,520,984 B1 * | 2/2003 | Garrison et al. | 623/1.11 |
| 6,547,814 B2 | 4/2003 | Edwin et al. | 623/1.13 |
| 6,547,815 B2 | 4/2003 | Myers | 623/1.13 |
| 6,558,414 B2 | 5/2003 | Layne | 623/1.13 |
| 6,558,415 B2 | 5/2003 | Thompson | 623/1.16 |
| 6,579,314 B1 * | 6/2003 | Lombardi et al. | 623/1.44 |
| 6,635,082 B1 * | 10/2003 | Hossainy et al. | 623/1.15 |
| 6,878,162 B2 * | 4/2005 | Bales et al. | 623/1.15 |
| 7,037,330 B1 * | 5/2006 | Rivelli et al. | 623/1.15 |
| 2001/0039446 A1 | 11/2001 | Edwin et al. | 623/1.13 |
| 2001/0044650 A1 | 11/2001 | Simso et al. | 623/1.16 |
| 2001/0049551 A1 | 12/2001 | Tseng et al. | 623/1.15 |
| 2002/0040237 A1 | 4/2002 | Lentz et al. | 623/1.13 |
| 2002/0055770 A1 | 5/2002 | Doran et al. | 623/1.15 |
| 2002/0091437 A1 | 7/2002 | Tseng et al. | 623/1.13 |
| 2002/0095205 A1 * | 7/2002 | Edwin et al. | 623/1.13 |
| 2002/0103528 A1 * | 8/2002 | Schaldach et al. | 623/1.15 |
| 2002/0193867 A1 * | 12/2002 | Gladdish et al. | 623/1.15 |
| 2003/0069630 A1 * | 4/2003 | Burgermeister et al. | 623/1.15 |
| 2003/0225448 A1 | 12/2003 | Gerberding | 623/1.15 |
| 2004/0015228 A1 * | 1/2004 | Lombardi et al. | 623/1.18 |
| 2004/0044399 A1 * | 3/2004 | Ventura | 623/1.16 |

FOREIGN PATENT DOCUMENTS

| | | |
|---|---|---|
| WO | WO 01/82833 | 11/2001 |
| WO | 02/22024 | 3/2002 |
| WO | 02/055120 | 7/2002 |

OTHER PUBLICATIONS

Canadian Office Action in related Canadian Patent Application No. 2,526,632. May 19, 2011 6 pgs.

Japanese Office Action in related Japanese Patent Application 2006-517112. Aug. 31, 2010. 12 pgs.

Canadian Office Action in related Canadian Patent Application 2,526,632. Aug. 19, 2010. 8 pgs.

* cited by examiner

SANDWICHED RADIOPAQUE MARKER ON COVERED STENT

BACKGROUND OF THE INVENTION

The use of endoprostheses is well known in maintaining the patency of bodily vessels and treating stenoses and aneurysms within arteries and other body spaces.

Recently, stents having coverings have been suggested for a variety of purposes including for the treatment of intracranial aneurysms. Covered stents, when used for this purpose, must be deployed with extreme precision. Typically, the covered portion of the stent must be deployed across the neck of the aneurysm, but not over bifurcations or side arteries.

There is a need for intracranial stents with markers which are readily visualized under imaging modalities such as fluoroscopy and which are placed so as to indicate the location of a covered portion of a stent in order to facilitate the precise deployment of such a stent.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent comprising a tubular framework having an outer surface and an inner surface and a plurality of interconnected struts. An outer covering extends along at least a portion of the outer surface of the expandable framework and an inner covering extends along at least a portion of the inner surface of the expandable framework. At least a portion of the inner and outer coverings are contiguous with one another. Desirably, the inner and outer coverings are coextensive with one another. The stent further comprises at least one radiopaque marker disposed between the inner covering and the outer covering. Desirably, the inner covering and the outer covering comprise PTFE. More desirably, the PTFE is in the form of expanded PTFE. Other suitable coating materials may be used.

The radiopaque marker may be in the form of a radiopaque marker band which is optionally wound about a portion of the stent It is also within the scope of the invention for the marker to be in the form of a plug. The marker may be embedded in a portion of the stent framework. The marker band may be crimped to the stent framework. Typically, the marker will not protrude beyond the inner and outer surfaces of the stent framework, although it is possible with some embodiments.

It is further within the scope of the invention for there to be a plurality of radiopaque markers. Typically, where a plurality of markers is present, at least some of the radiopaque markers indicate at least one end of the covering on the inner and outer surfaces and desirably both ends.

In accordance with the invention, the stent may be sized for use in any bodily vessel. In one embodiment, the stent is sized for used in a cranial vessel.

In another embodiment, the invention is directed to a stent comprising a tubular framework having an outer surface and an inner surface and a plurality of interconnected struts. An outer covering of PTFE extends along at least a portion of the outer surface of the expandable framework and an inner covering of PTFE extends along at least a portion of the inner surface of the expandable framework. At least a portion of the inner and outer coverings are contiguous with one another. Desirably, the inner and outer coverings are coextensive with one another. The stent further comprises at least one marker which is radiopaque or which may be visualized using magnetic resonance imaging. The marker is disposed between the inner covering and the outer covering. Desirably, the PTFE is in the form of expanded PTFE.

The invention is also directed to a method of manufacturing a stent comprising the steps of providing a stent framework comprising a plurality of interconnected struts, the framework having an inner surface and an outer surface, providing radiopacity to the stent framework in a desired region of the framework, covering the inner surface of the stent framework in the desired region of the stent framework with PTFE and covering the outer surface of the stent framework in the desired region of the stent framework with PTFE. Optionally, the method may further comprise the steps of providing radiopacity to the stent framework in a plurality of desired regions and covering the outer and inner surfaces of the stent framework with PTFE in each of the desired regions.

In accordance with the invention, the radiopacity may be provided via radiopaque markers which are attached to the stent framework. Each radiopaque marker may be in the form of a radiopaque material which is wound around a portion of the stent framework. It is also within the scope of the invention for each radiopaque marker to be in the form of a radiopaque plug which is inserted into an opening in the stent framework. Optionally, the radiopacity may be provided in the form of one or more markers which mark one or more ends of the PTFE on the inner and outer surface of the stent. Desirably, the PTFE on the inner and outer surfaces of the stent will be coextensive with one another.

It is within the scope of the invention for the PTFE on the inner surface to be provided in the form of a first extruded tube of expanded PTFE and the PTFE on the outer surface to be provided in the form of a second extruded tube of expanded PTFE.

These and other embodiments which characterize the invention are pointed out with particularity in the claims annexed hereto and forming a part hereof. However, for a better understanding of the invention, its advantages and objectives obtained by its use, reference should be made to the drawings which form a further part of the disclosure.

BRIEF DESCRIPTION OF THE DRAWING(S)

A detailed description of the invention is hereafter described with specific reference being made to the drawings.

FIG. 1b is a schematic illustration of a cross-section of stent similar to that of FIG. 1a.

DETAILED DESCRIPTION OF THE INVENTION

Figure 1A:
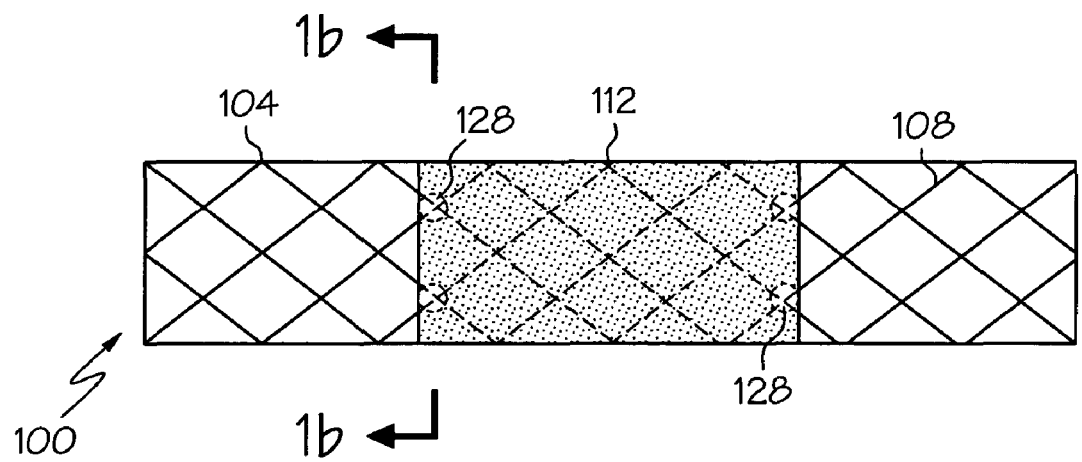
FIG. 1a shows a schematic of a side view of a stent in accordance with the instant invention with portions cut away to show the markers.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In one embodiment, the invention is directed to a stent comprising a tubular framework having an outer surface and an inner surface and a plurality of interconnected struts. A non-limiting example of such a stent is shown in a schematic view generally at 100 in FIGS. 1a and 1b. Stent 100 includes framework 104 which is comprised of a plurality of interconnected struts 108. The invention is not limited to the framework shown in FIG. 1a. Other frameworks, including any of those disclosed in patent publication US 20020055770 may be used. More generally, the framework may be in the form of a plurality of serpentine bands 106 which are connected to one another at a plurality of locations, as shown by way of example in FIG. 1c. Even more generally, the framework may be in the form of a tube with openings of any shape therethrough An outer covering 112 extends along at least a portion of the outer surface 116 of the expandable framework and an inner covering 120 extends along at least a portion of the inner surface 124 of the expandable framework. At least a portion of the inner and outer coverings are contiguous with one another. Desirably, as shown in FIG. 2, inner covering 120 and outer covering 112 are coextensive with one another.

The inner covering 120 and outer covering 112 may be any material suitable to be used in a covered stent. Example materials include polymers and polymer carriers such as urethanes, silicone, and the like; tissue coverings such as fixed subendothelium and internal elastic lamina of porcine vessels; biocompatible metallic films such as Nitinol, stainless steel, tantalum, gold, platinum, copper and various alloys; fabrics; and suitable combinations of such materials. Desirably, the inner covering 120 and outer covering 112 comprise PTFE. More desirably, the PTFE is in the form of expanded PTFE.

Figure 1B:
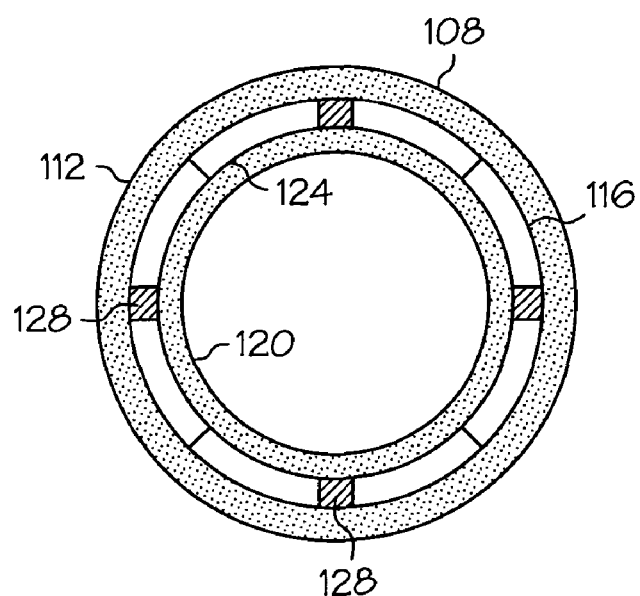
Figure 1C:
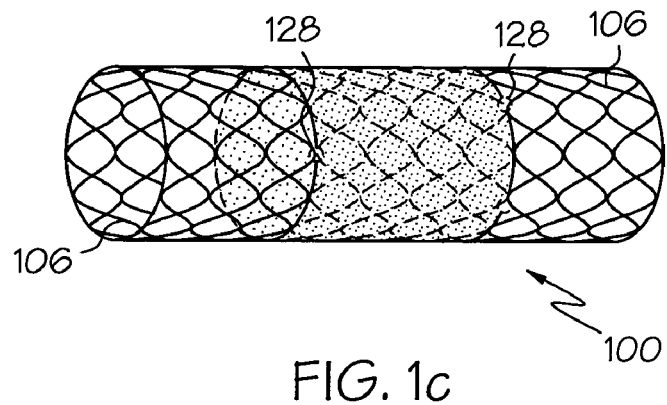
FIG. 1c shows a perspective view of a stent in accordance with the instant invention with portions cut away to show the markers.
Figure 5:
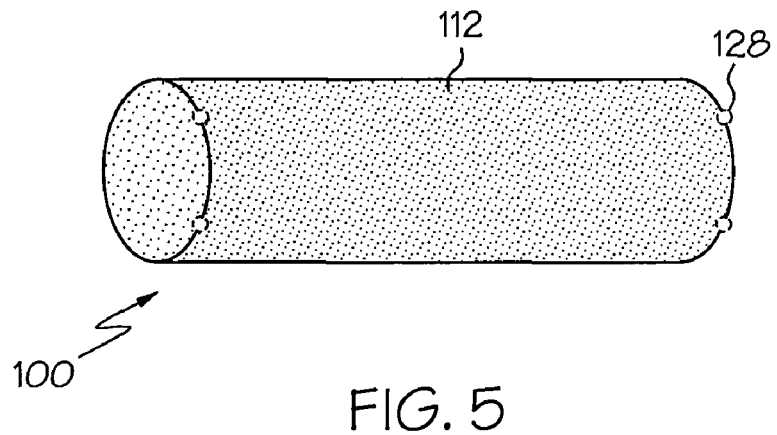
FIG. 5 shows a fully covered inventive stent having radiopaque cover markers.
Figure 6:
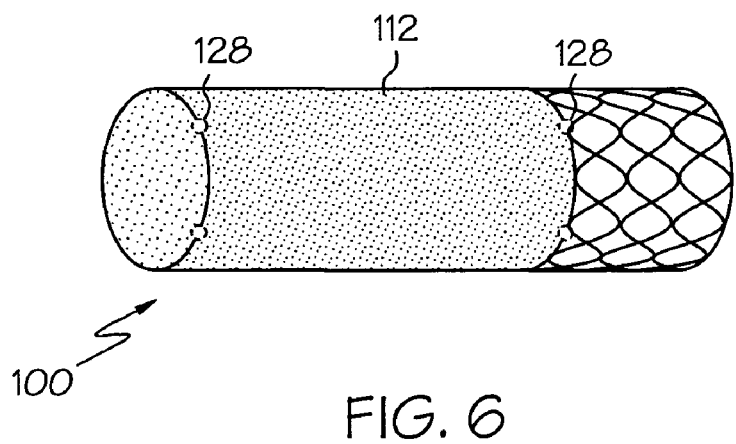
FIG. 6 shows a partially covered inventive stent having radiopaque cover markers.

As shown in FIGS. 1a and 1b, outer covering 112 and inner covering 120 extend over a portion, but not the entirety of the stent, with the ends of the stent not being covered. In another embodiment of the invention, the inner and/or outer covering(s) may extend from a proximal end region to a distal end region of the stent, as depicted in FIG. 5. In other embodiments, either or both of the coverings may extend from a proximal end region to an intermediate portion of the stent, as shown in FIG. 6, or from a distal end region to an intermediate portion of the stent. Other arrangements of the coverings are also within the scope of the invention.

Figure 2:
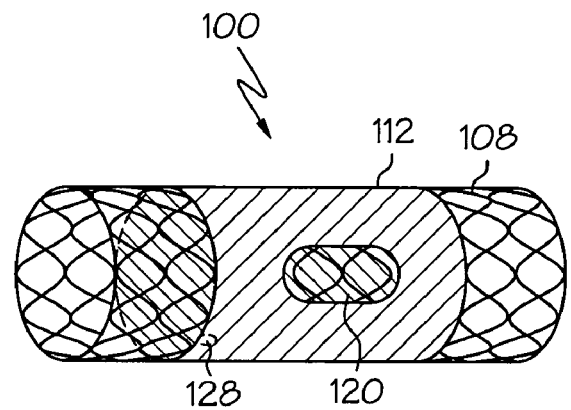
FIG. 2 shows a perspective view of another embodiment of the instant invention with parts cut away illustrating, among other things, that the inner and outer coverings are coextensive with one another.

As shown in FIGS. 1 and 2, the stent further comprises at least one and desirably, a plurality of radiopaque markers 128 disposed between the inner covering 120 and the outer covering 112.

Figure 3A:
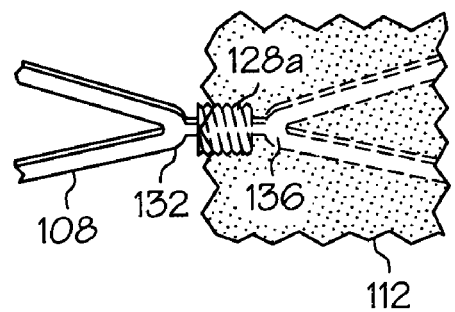
FIGS. 3a-3c show several radiopaque markers which may be used in the instant invention.
Figure 3B:
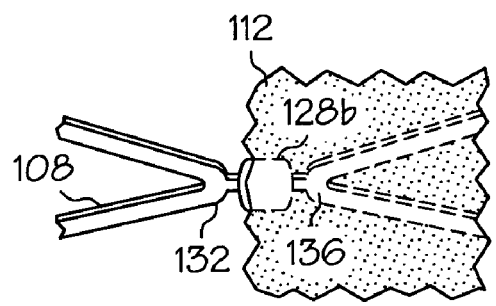
Figure 3C:
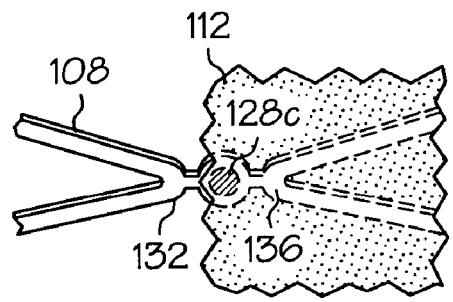

The radiopaque marker may be in the form of a radiopaque marker band 128a which is optionally wound or coiled about a portion of the stent, as shown in FIG. 3a. Other examples of such an arrangement are disclosed in U.S. Pat. No. 5,683,450. It is within the scope of the invention for the radiopaque marker to be crimped onto a portion of the stent framework. As shown in FIG. 3b, the marker is in the form of a split tube 128b which is crimped onto a portion of the stent framework. It is also within the scope of the invention for the marker to be in the form of a plug of material. As shown in FIG. 3c, radiopaque marker 128c, in the form of a plug, is disk-like. In some embodiments, as shown in FIG. 3c, the marker will be embedded in a portion of the stent framework. Desirably, as is the case with the stent of FIG. 3c, the marker will not protrude beyond the inner and outer surfaces of the stent framework. It is also within the purview of the invention to utilize markers that may protrude beyond the stent framework surfaces, as is often the case with radiopaque windings or crimped markers.

In the embodiments of FIGS. 3a-3c, the radiopaque markers are shown attached to the stent framework in the region of a strut which connects a peak 132 on one serpentine band to a trough 136 on another serpentine band. It is also within the scope of the invention for the radiopaque markers to be provided within or along a circumferential band of the stent framework.

It is further within the scope of the invention for there to be a plurality of radiopaque markers 128, as shown by way of example, in FIGS. 1a, 1b and 5-7. Typically, where a plurality of markers is present, at least some of the radiopaque markers indicate at least one end of the coverings on the inner and outer surfaces and desirably both ends.

Figure 7:
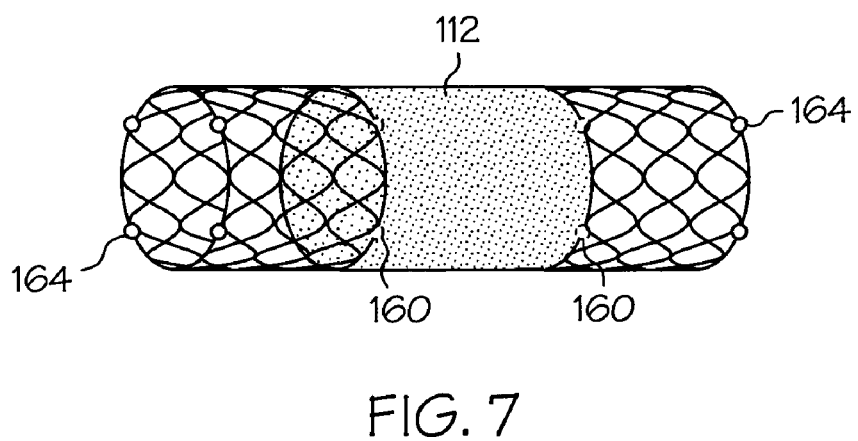
FIG. 7 shows a partially covered inventive stent having both radiopaque cover markers and radiopaque end markers.

Additionally, radiopaque markers may be used to denote end portions of the stent. FIG. 7 shows an inventive stent 100 having both cover markers 160 and end markers 164. Cover markers 160 and end markers 164 may be made from the same material or from different materials, and the method of securement of the markers to the stent may vary between marker type, and even between markers of the same type.

The radiopaque markers may be made of any suitable radiopaque material including, but not limited to a metal from the group consisting of gold, platinum, silver, titanium, tantalum, niobium, molybdenum, rhodium, palladium, hafnium, tungsten and iridium.

In accordance with the invention, the stent may be sized for use in any bodily vessel. In one embodiment, the stent is sized for use in a cranial vessel. In this embodiment, the inner and outer coverings are typically confined to a portion of the stent with the first and second ends of the stent framework remaining uncovered, as shown in FIGS. 1a and 4.

Figure 4:
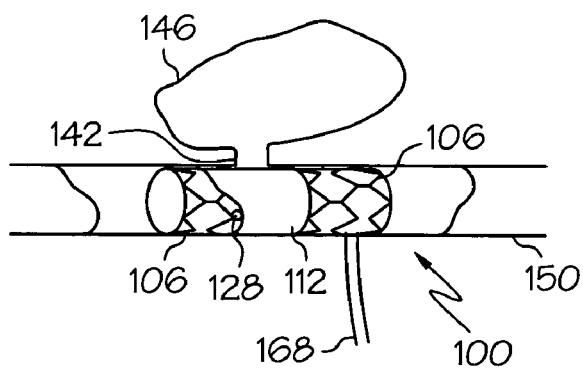
FIG. 4 illustrates a vessel with an aneurysm, portions of the vessel cut away, with a stent deployed therein in accordance with an embodiment of the invention.

FIG. 4. depicts a stent 100 deployed in a vessel 150 with the covering 112 of the stent 100 deployed across the neck 142 of an aneurysm 146. Uncovered regions located at the ends of the stent 100 are desirable to anchor the ends of the stent 100 beyond the aneurysm neck 142. Further, regions without covering 112 allow for continued blood flow through any bifurcations or side branch arteries 168 in proximity to the stent uncovered region. It is desirable to provide uncovered end regions sufficient to anchor the stent 100 securely. For stents deployed into a cranial vessel to treat aneurysms, each uncovered region located at an end of the stent is desirably two to four millimeters long, measured along the longitudinal axis of the stent, although the uncovered region length may be longer or shorter depending upon the particular application.

In one embodiment, the invention is directed to a stent comprising a tubular framework having an outer surface and an inner surface and a plurality of interconnected struts. An outer covering extends along at least a portion of the outer surface of the expandable framework and an inner covering extends along at least a portion of the inner surface of the expandable framework. At least a portion of the inner and outer coverings are contiguous with one another. Desirably, the inner and outer coverings are coextensive with one another. The stent further comprises at least one marker which is radiopaque or which may be visualized using magnetic resonance imaging (MRI). The marker is disposed between the inner covering and the outer covering. Desirably, the inner covering and outer covering comprise PTFE. More desirably, the PTFE is in the form of expanded PTFE. Suitable markers for MRI include materials which incorporate paramagnetic species such as Gadolinium-DTPA (diethylene triamine pentaacetic acid) chelates as disclosed in U.S. Pat. No. 6,361,759.

The invention is also directed to a method of manufacturing a stent comprising the steps of providing a stent framework comprising a plurality of interconnected struts, the framework having an inner surface and an outer surface, providing radiopacity to the stent framework in a desired region of the framework, covering the inner surface of the stent framework in the desired region of the stent framework with an appropriate covering material and covering the outer surface of the stent framework in the desired region of the stent framework with an appropriate covering material. Optionally, the method may further comprise the steps of providing radiopacity to the stent framework in a plurality of desired regions and covering the outer and inner surfaces of the stent framework with covering material in each of the desired regions. Desirably, the inner covering and outer covering comprise PTFE. More desirably, the PTFE is in the form of expanded PTFE.

In accordance with the invention, the radiopacity may be provided via radiopaque markers which are attached to the stent framework. Each radiopaque marker may be in the form of a radiopaque material which is wound around a portion of the stent framework. It is also within the scope of the invention for each radiopaque marker to be in the form of a radiopaque plug which is inserted into an opening in the stent framework. Optionally, the radiopacity may be provided in the form of one or more markers which mark one or more ends of the covering material on the inner and outer surface of the stent. Desirably, the covering material on the inner and outer surfaces of the stent will be coextensive with one another.

It is within the scope of the invention for the PTFE on the inner surface to be provided in the form of a first extruded tube of expanded PTFE (ePTFE) and the PTFE on the outer surface to be provided in the form of a second extruded tube of ePTFE. The first and second extruded tubes of ePTFE are desirably bonded to the stent in the following manner. The ePTFE inner covering 120 is first placed over a perforated steel tube. The framework 104 is circumferentially placed over the ePTFE inner covering 120, and the ePTFE outer covering 112 is circumferentially placed over the framework 104. The entire assembly is then subject to heat and pressure sufficient to laminate the inner covering 120 and outer covering 112 at their common areas, thus securing the ePTFE to the framework 104.

The above method of bonding the ePTFE layers to the stent is desirable because the inner covering 120 and outer covering 112 unite, and because no adhesives are required in the assembly process. Any other methods of securing ePTFE to the stent that are known in the art may be utilized, including any of the techniques disclosed in U.S. Pat. Nos. 6514283, 6451047 and 6139573.

This invention is applicable to self-expanding stents as well as to mechanically expandable stents and hybrid stents which are both mechanically expandable and self-expanding.

If the stent is manufactured from a shape-memory alloy, such as Nitinol, following the lamination process the stent may be cooled in liquid nitrogen, wherein the metal is thermally transformed to a martinsitic state, and the stent may be easily compressed and inserted into a deployment sheath of a delivery catheter.

The stent framework may be made of any suitable stent material, whether polymeric or metal or otherwise. It may be of shape memory alloy such as Nitinol or the like, or of stainless steel, titanium, tantalum, gold, platinum, copper and the like or alloys of these metals. The struts of the framework may be of any suitable cross-section.

The inventive stents may also be provided with various bio-compatible coatings to enhance various properties of the stent. For example, the inventive stents may be provided with lubricious coatings. The inventive stents may also provide drug release over time. This release of drugs over time may be provided through drug-containing coatings, or direct implantation of a drug onto or into the coverings of the stent, or drug-containing coatings applied prior to applying the coverings.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon or delivery catheter during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anticoagulants such as D-Phe-Pro-Arg chloromethyl keton, an RGD peptide-containing compound, heparin, antithrombin compounds, platelet receptor antagonists, antithrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha. and beta., platelet-derived endothelial growth factor, platelet-derived growth factor, tumor necrosis factor .alpha., hepatocyte growth factor and insulin like growth factor, cell cycle inhibitors including CD inhibitors, thymidine kinase ("TK") and other agents useful for interfering with cell proliferation the family of bone morphogenic proteins ("BMP's"),BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL.RTM.), fibrin, collagen and derivatives thereof, polysaccharides such as celluloses, starches, dextrans, alginates and derivatives, hyaluronic acid, squalene emulsions. Polyacrylic acid, available as HYDROPLUS.RTM. (Boston Scientific Corporation, Natick, Mass.), and described in U.S. Pat. No. 5,091,205 is particularly desirable. Even more desirable is a copolymer of polylactic acid and polycaprolactone.

The inventive stents may find use in cerebral vessels, in coronary arteries, renal arteries, peripheral arteries including iliac arteries, arteries of the leg aorta, and arteries of the neck. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

The inventive stent may be delivered on a catheter. The nature of the catheter will depend on whether the stent is balloon expandable or self-expanding.

The stent frameworks used in the inventive stents disclosed herein may be manufactured using any suitable known manufacturing technique including laser cutting or mechanically cutting a pattern in a sheet of material and rolling the material, mechanically cutting, etching, chemically or otherwise or laser cutting a stent pattern in a tube of material, or using an EDM (electrical discharge machining) technique to cut a stent pattern into a sheet of material or a tube of material.

The invention is further directed to a method of treating an aneurysm, desirably a cerebral aneurysm using any of the inventive stents disclosed herein. Typically, the stent will be delivered via catheter to a region in a vessel having an aneurysm. As shown in FIG. 4, the stent 100 is deployed in a vessel 150 with the covering 112 of the stent 100 deployed across the neck 142 of an aneurysm 146, but not restricting blood flow through any bifurcations or side branch arteries 168.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent comprising a single tubular framework having an outer surface and an inner surface and a plurality of interconnected struts, the struts comprising a plurality of serpentine bands and further comprising a generally linear connector strut attaching a peak of one serpentine band to a trough of an immediately adjacent serpentine band at the respective apices of each of the peak and the trough, wherein the respective apices of the immediately adjacent serpentine bands are axially aligned and connected with each other in opposing directions such that the single tubular framework has no gaps between the respective apices of the immediately adjacent serpentine bands, and wherein the opposing apices reduce a distance between the immediately adjacent serpentine bands and attach to the generally linear connector strut, the framework further comprising an outer covering of PTFE and an inner covering of PTFE, the outer covering extending along at least a portion of the outer surface of the expandable framework, the inner covering extending along at least a portion of the inner surface of the expandable framework, at least a portion of the inner and outer coverings being contiguous, the stent further comprising at least one radiopaque marker of a first set that is directly and only attached to the plurality of interconnected struts at the generally linear connector strut and disposed between the inner covering and the outer covering and placed to indicate a deployed position of a covered region of the stent, the framework further comprising a circumferential non-serpentine band at least one distal end of an uncovered region of the framework comprising at least one radiopaque marker of a second set placed to indicate a deployed position of the uncovered region of the stent.

2. The stent of claim 1 wherein the PTFE is in the form of expanded PTFE.

3. The stent of claim 1 wherein at least one radiopaque marker of the first set is in the form of a radiopaque marker band.

4. The stent of claim 3 wherein the marker band is wound about a portion of the connector strut.

5. The stent of claim 3 wherein the marker band is a split tube crimped to the connector strut.

6. The stent of claim 1 wherein at least one radiopaque marker of the first set is embedded in a portion of the connector strut.

7. The stent of claim 1 wherein at least one radiopaque marker of the first set is located adjacent an uncovered region of the stent.

8. The stent of claim 1 wherein the connector strut comprises an opening in which a disk-like radiopaque plug is embedded.

9. The stent of claim 1 comprising a plurality of radiopaque markers.

10. The stent of claim 9 wherein the PTFE is in the form of expanded PTFE.

11. The stent of claim 10 wherein the PTFE on the outer surface and the PTFE on the inner surface of the framework are coextensive with one another.

12. The stent of claim 11 wherein at least some of the radiopaque markers of the first set indicate at least one end of the PTFE on the inner and outer surfaces.

13. The stent of claim 12 wherein the radiopaque markers of the first and second set do not protrude beyond the outer surface and inner surfaces of the stent framework.

14. The stent of claim 11 wherein at least some of the radiopaque markers of the first set indicate a first end of the PTFE on the inner and outer surfaces and others of the radiopaque markers indicate a second end of the PTFE on the inner and outer surfaces.

15. The stent of claim 14 sized for use in a cranial vessel.

16. The stent of claim 14 wherein the radiopaque markers of the first and second set do not protrude beyond the outer surface and inner surfaces of the stent framework.

17. The stent of claim 11 wherein the radiopaque markers of the first and second set do not protrude beyond the outer surface and inner surfaces of the stent framework.

18. The stent of claim 1 sized for use in a cranial vessel.

19. The stent of claim 1 wherein the radiopaque markers of the first and second set do not protrude beyond the outer surface and inner surfaces of the stent framework.

20. A stent comprising a single tubular framework having an outer surface and an inner surface and a plurality of interconnected struts, the struts comprising a plurality of serpentine bands and further comprising a generally linear connector strut attaching a peak of one serpentine band to a trough of an immediately adjacent serpentine band at the respective apices of each of the peak and the trough, wherein the respective apices of the immediately adjacent serpentine bands are axially aligned and connected with each other in opposing directions such that the single tubular framework has no gaps between the respective apices of the immediately adjacent serpentine bands, and wherein the opposing apices reduce a distance between the immediately adjacent serpentine bands and attach to the generally linear connector strut, the framework further comprising an outer covering of PTFE and an inner covering of PTFE, the outer cover extending along at least a portion of the outer surface of the framework, at least a portion of the inner and outer coverings being contiguous, the generally linear connector strut having at least one marker of a first set which is radiopaque or which may be visualized using magnetic resonance imaging, the marker of the first set directly and only attached to the plurality of interconnected struts at the generally linear connector strut and disposed between the inner coverings and the outer coverings and placed to indicate a deployed position of a covered region of the stern, the framework further comprising a circumferential non-serpentine band at least one distal end of an uncovered region of the framework comprising at least one radiopaque marker of a second set placed to indicate a deployed position of the uncovered region of the stent.

21. A covered stent comprising:
a single tubular stent framework having an interior surface, an exterior surface and a first marker region, the framework comprising a plurality of serpentine bands and further comprising a generally linear connector strut attaching a peak of one serpentine band to a trough of an immediately adjacent serpentine band at the respective apices of each of the peak and the trough, wherein the respective apices of the immediately adjacent serpentine bands are axially aligned and connected with each other in opposing directions such that the single tubular framework has no gaps between the respective apices of the immediately adjacent serpentine bands, and wherein the opposing apices reduce a distance between the immediately adjacent serpentine bands and attach to the generally linear connector strut;
at least one radiopaque marker located within the first marker region of said framework, the marker directly and only attached to the plurality of serpentine bands at the generally linear connector strut and placed to indicate a deployed position of a covered region of the stent;
a circumferential non-serpentine band at least one distal end of an uncovered region of the framework comprising at least one radiopaque marker of a second marker region placed to indicate a deployed position of the uncovered region of the stent; and
a covering of expanded PTFE covering the interior surface and exterior surface of said framework in the first marker region.

22. A stent comprising a single tubular expandable framework having an outer surface and an inner surface, the tubular expandable framework comprising a plurality of serpentine bands, immediately adjacent serpentine bands having axially aligned and connected oppositely pointing apices such that the single tubular framework has no gaps between the respective apices of the immediately adjacent serpentine bands, wherein the oppositely pointing apices reduce a distance between the immediately adjacent serpentine bands, said framework further including linear connecting members connecting at least some of said oppositely pointing apices of the immediately adjacent serpentine bands, an outer covering of PTFE and an inner covering of PTFE, the outer covering extending along at least a portion of the outer surface of the expandable framework, the inner covering extending along at least a portion of the inner surface of the expandable framework, at least a portion of the inner and outer coverings being contiguous, the stent further comprising at least one radiopaque marker of a first set that is directly and only attached to the plurality of serpentine bands at the generally linear connecting members and disposed between the inner covering and the outer covering and placed to indicate a deployed position of a covered region of the stent, the framework further comprising a circumferential non-serpentine band at least one distal end of an uncovered region of the framework comprising at least one radiopaque marker of a second set placed to indicate a deployed position of the uncovered region of the stent.

23. The stent of claim 22, wherein both the inner covering and the outer covering do not extend along at least a portion of the expandable framework.

24. The stent of claim 22, wherein the expandable framework extends beyond both the inner covering and the outer covering.

25. The stent of claim 22, wherein at least a portion of the inner covering is laminated to at least a portion of the outer covering.

* * * * *

UNITED STATES PATENT AND TRADEMARK OFFICE
CERTIFICATE OF CORRECTION

| | | |
|---|---|---|
| PATENT NO. | : 8,021,418 B2 | Page 1 of 1 |
| APPLICATION NO. | : 10/600022 | |
| DATED | : September 20, 2011 | |
| INVENTOR(S) | : Brent C. Gerberding et al. | |

It is certified that error appears in the above-identified patent and that said Letters Patent is hereby corrected as shown below:

Title Page, Item (75) Inventors, line 2, delete "Bavesh" and insert --Bhavesh-- therefor.

Signed and Sealed this
Twenty-second Day of November, 2011

David J. Kappos
*Director of the United States Patent and Trademark Office*